(12) United States Patent
Knaan et al.

(10) Patent No.: US 7,717,561 B2
(45) Date of Patent: May 18, 2010

(54) SIGHT LINE DETECTING METHOD

(75) Inventors: Dotan Knaan, Jerusalem (IL); Adi Shavit, Jerusalem (IL); Dana Shavit, Jerusalem (IL); Kazufumi Suzuki, Tokyo (JP); Norio Ichihashi, Tokyo (JP); Akio Takahashi, Saitama (JP); Akihito Kimata, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 217 days.

(21) Appl. No.: 11/664,210

(22) PCT Filed: Sep. 29, 2005

(86) PCT No.: PCT/JP2005/017987

§ 371 (c)(1),
(2), (4) Date: Feb. 8, 2008

(87) PCT Pub. No.: WO2006/035890

PCT Pub. Date: Apr. 6, 2006

(65) Prior Publication Data

US 2009/0015788 A1    Jan. 15, 2009

(30) Foreign Application Priority Data

Sep. 29, 2004  (JP) .............................. 2004-283456

(51) Int. Cl.
*A61B 3/14* (2006.01)

(52) U.S. Cl. ...................... 351/210; 351/206; 351/209; 396/51

(58) Field of Classification Search ................. 351/206, 351/208–210; 396/51
See application file for complete search history.

(56) References Cited

U.S. PATENT DOCUMENTS 5,889,577 A * 3/1999 Kohayakawa ............... 351/211

(Continued)

FOREIGN PATENT DOCUMENTS

| JP | 08-297019 | 11/1996 |
|---|---|---|
| JP | 10-334274 | 12/1998 |

OTHER PUBLICATIONS

Ohno et al., An Eyeball-Model-Based Eye Tracking Method, "Eighth Image Sensing Symposium", pp. 307-312, NTT Communication Science Laboratories, NTT Corp., Japan, 2002.

(Continued)

*Primary Examiner*—Jordan M. Schwartz
(74) *Attorney, Agent, or Firm*—Carrier, Blackman & Associates P.C.; Joseph P. Carrier; William D. Blackman

(57) ABSTRACT

In a sight line vector detecting system comprising: an infrared light source for illuminating either an eye or a face; a camera for photographing either the eye or the face; and a computer for processing photographed image data of said camera so as to calculate a sight line vector, the computer includes an image processing unit for detecting the true luminance point and the center of the pupil from the photographed image data; and a calculating unit for calculating the sight line vector; and the image processing unit performs such a processing operation that the image processing unit determines a luminance point capable of satisfying a predetermined requirement as the true luminance point among luminance points having the pupils at near places, calculates a center of the pupils, and further, calculates a center of a cornea ball.

15 Claims, 7 Drawing Sheets

U.S. PATENT DOCUMENTS

| | | | |
|---|---|---|---|
| 5,987,151 A * | 11/1999 | Akashi | 382/100 |
| 6,426,740 B1 * | 7/2002 | Goto et al. | 345/157 |
| 6,507,702 B2 * | 1/2003 | Ohtani | 396/50 |
| 7,401,920 B1 * | 7/2008 | Kranz et al. | 351/210 |
| 2004/0174496 A1 * | 9/2004 | Ji et al. | 351/209 |
| 2005/0200806 A1 * | 9/2005 | Knaan et al. | 351/169 |

OTHER PUBLICATIONS

Ohno et al., An Eye Tracking System Based on Eye Ball Model—Toward Realization of Gaze Controlled Input Device-, "Information Processing Research Report 2001-HI-93", pp. 47-54, NTT Communications Science Laboratories, Japan.

* cited by examiner

SIGHT LINE DETECTING METHOD

CROSS-REFERENCE TO RELATED APPLICATIONS

The present application is a U.S. National phase of, and claims priority based on PCT/JP2005/017987, filed 29 Sep. 2005, which, in turn, claims priority from Japanese patent application 2004-283456, filed 29 Sep. 2004. The entire disclosure of each of the referenced priority documents is incorporated herein by reference.

TECHNICAL FIELD

The present invention relates to a technique for detecting a line of sight. More specifically, the present invention is directed to a sight line detecting method and a sight line detecting apparatus for a person who wears spectacles.

BACKGROUND ART

Conventionally, technical ideas for detecting lines of sight have been developed as computer input apparatuses designed for handicapped persons who cannot freely use their hands or their fingers. Also, detections of sight lines have been utilized as vehicle assisting means, while sight lines of car drivers are monitored. However, conventional sight line detecting apparatuses have been designed for mounting specific instruments on users, and these sight line detecting technical ideas constrain these users. As a result, there is such a problem that these conventional sight line detecting apparatuses are not so user-friendly. In order to solve this problem, very recently, technical ideas capable of detecting lines of sight (LOS) have been developed by using eyeball models.

In the case that the eyeball models are utilized, correct distances from camera positions up to face surfaces are calculated by simple methods in correct manners, resulting in one problem. For example, the apparatus described in Japanese Laid-open Patent Application No. Hei-8-297019 (vehicle-purpose sight line direction measuring apparatus) (will be referred to as "patent publication 1" hereinafter) corresponds to such an apparatus for detecting a sight line of a car driver, while a distance sensor is utilized as means for acquiring a distance from a position of a camera to a face surface of the driver. As the distance sensor, an ultrasonic type sensor, and the like are used. When the ultrasonic type sensor is employed, the following problems occur. That is, the entire sight line detecting apparatus becomes complex; the distance detecting precision is deteriorated if the simple sensor is employed; and if the detecting precision is increased, then the cost of the entire line detecting apparatus is increased.

Also, Information Processing Research Report 2001-HI-93, pages 47 to 54 (Sight Line Measuring System based upon Eyeball Shaped Model), and Eighth Image Sensing Symposium, pages 307 to 312, 2002 (Sight Line Measuring Method based upon Eyeball Model) (will be referred to as "non-patent publications 1 and 2" hereinafter) describe technical ideas capable of detecting directions as to lines of sight (LOS) by utilizing eyeball models. In the apparatuses of these publications, a distance from a camera (otherwise, point light source) up to a face surface must be measured in order that a near-infrared light is illuminated from the point light source to a cornea present in an eye so as to acquire coordinates of a reflection image (called as "Purkinje image"). As the distance measuring method, this distance is measured based upon a focusing value when a lens of the camera is focused on such a position that a dimension of the point light source (namely, dimension of Purkinje image) on an image photographed by the camera becomes minimum. However, it is practically difficult to adjust that the dimension of the Purkinje image correctly becomes minimum. As a consequence, the high-precision distance measurement cannot be expected, but also, the sight line direction by utilizing this measured distance contains errors, resulting in another problem. The Applicant of the present invention has already filed the invention capable of solving these problems (U.S. patent application Ser. No. 11/078,144, "LINE-OF-SIGHT DETECTING METHOD AND APPARATUS THEREFOR" filed on Mar. 11, 2005) (will be referred to as "patent publication 2" hereinafter).

DISCLOSURE OF THE INVENTION

Problems that the Invention is to Solve

However, the above-explained conventional techniques utilizing the eyeball models and the technical idea described in the patent publication 2 are directed to the persons who wear no spectacles, and thus, when these conventional techniques and disclosed technical idea are directly applied to persons who wear spectacles, there is such a risk that a large error may occur. In other words, even if an infrared light is illuminated to a cornea contained in an eye as a light source so as to acquire a reflection image, then a portion of the infrared light is reflected on lenses, or metal instruments of spectacles, so that a plurality of luminance points may appear in a photographed image in addition to a luminance point produced by reflecting the infrared light on an eyeball. Also, another problem may be conceived. That is, images which have passed through the spectacles are deviated, so that centers of pupils are not made coincident with luminance points.

The present invention has been made to solve the above-explained problems, and therefore, has an object to provide a sight line vector detecting system which can also be applied to a person who wears spectacles.

Means for Solving the Problems

The present invention has employed the below-mentioned arrangements as a means for solving the above-described problems. That is, a first sight line vector detecting system is featured by comprising: an infrared light source for illuminating either an eye or a face; a camera for photographing either the eye or the face; and a computer for processing photographed image data of the camera so as to calculate a sight line vector; in which the computer detects a true luminance point and a center of a pupil from the photographed image data so as to calculate the sight line vector.

Also, a second sight line vector detecting system is featured by that in the first sight line vector detecting system, the photographing camera is installed at a front view of the face of the person to be photographed, and at a position lower than the position of the eye.

Also, a third sight line vector detecting system is featured by that in the first, or second sight line vector detecting system, the infrared light source is installed at a position separated from an optical axis of the photographing camera in such a manner that a dark pupil effect is produced.

Also, a fourth sight line vector detecting system is featured by that in the first to third sight line vector detecting systems, the infrared light source is installed at a position lower than the photographing camera.

Also, a fifth sight line vector detecting system is featured by that in the first to fourth sight line vector detecting systems, the infrared light source is provided on both a right side and a left side of the optical axis of the photographing camera.

Also, a sixth sight line vector detecting system is featured by that in the first to fifth sight line vector detecting systems, the computer includes an image processing unit for detecting the true luminance point and the center of the pupil from the photographed image data; and a calculating unit for calculating the sight line vector; and in which the image processing unit performs such a processing operation that the image processing unit determines a luminance point capable of satisfying a predetermined requirement as the true luminance point among luminance points having the pupils at near places, calculates a center of the pupils, and further, calculates a center of a cornea ball by utilizing data obtained based upon the knowledge of the morphology.

Also, a seventh sight line vector detecting system is featured by that in the first to sixth sight line vector detecting systems, the calculating unit calculates the sight line vector based upon the center of the pupil and the center of the cornea ball.

Also, an eighth sight line vector detecting system is featured by that in the first to seventh sight line vector detecting systems, the computer further comprises: a preprocessing unit for preprocessing the photographed image data.

Also, a first sight line detecting method is featured by such a sight line vector detecting method with employment of a sight line detecting system equipped with an infrared light source for illuminating either an eye or a face, a camera for photographing either the eye or the face, and a computer for processing photographed image data of the camera so as to calculate a sight line vector, comprising: a detecting step for detecting a true luminance point and a center of a pupil from the photographed image data; and a calculating step for calculating a sight line vector.

A second sight line detecting method is featured by that in the first sight line detecting method, the detecting step comprises: a step for determining a luminance point capable of satisfying a predetermined requirement as the true luminance point among luminance points having the pupils at near places, and for calculating a center of the pupils; and a step for calculating a center of a cornea ball by utilizing data obtained based upon the knowledge of the morphology.

A third sight line detecting method is featured by that in the second sight line detecting method, the calculating step calculates the sight line vector based upon the center of the pupil and the center of the cornea ball.

A fourth sight line detecting method is featured by that in the first sight line detecting method, a step for preprocessing the photographed image data is provided before the detecting step.

Advantages of the Invention

In accordance with the present invention, there is such an advantage that the sight line vector can be correctly calculated within a practical range with respect to a user who wears spectacles.

Figure 1:
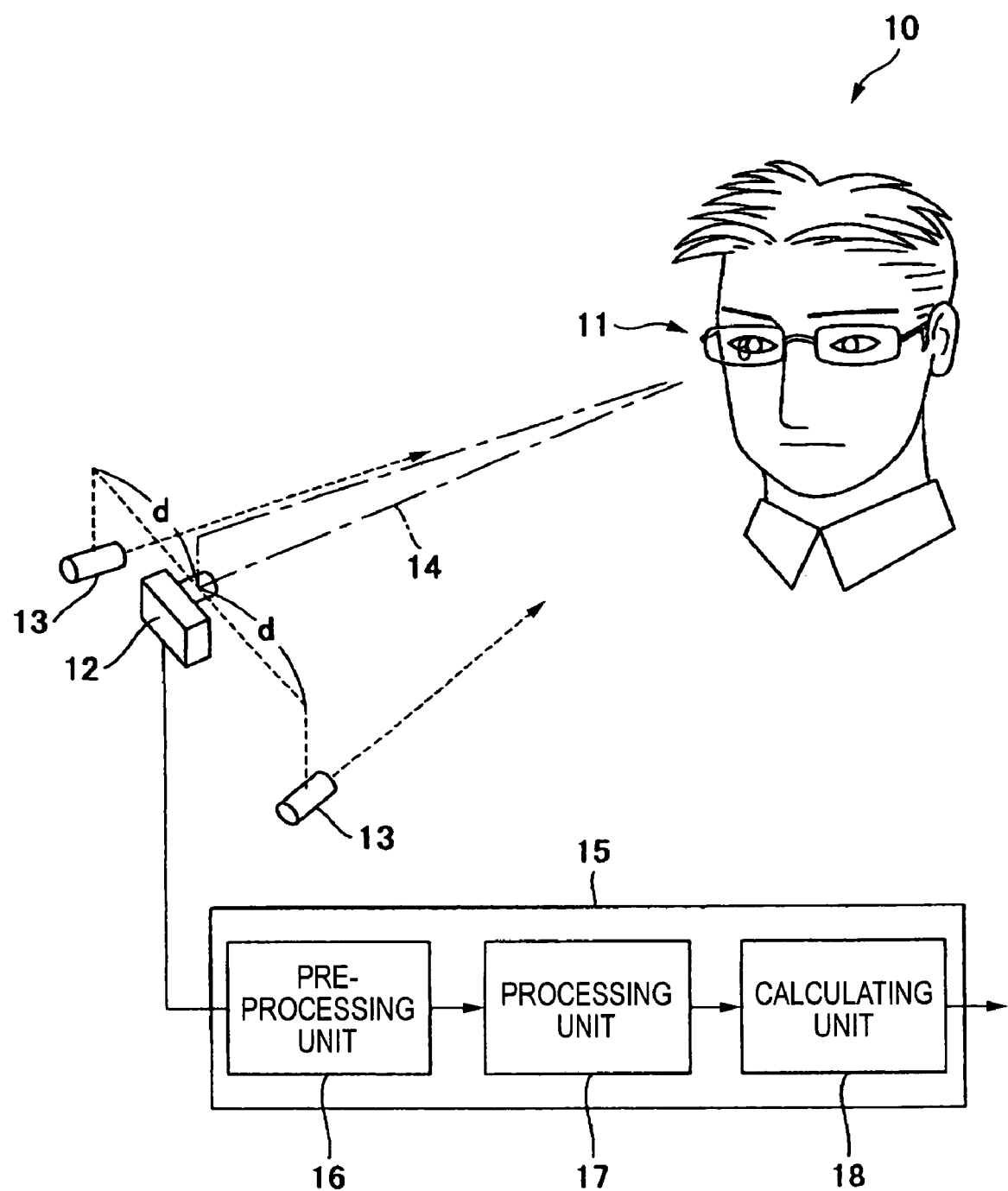
FIG. 1 shows an arrangement of a present embodiment mode (sight line vector detecting system).

DESCRIPTION OF REFERENCE NUMERALS AND SIGNS person to be photographed 10
spectacles 11
photographing camera 12
infrared light source 13
camera axis 14
computer 15
lens 22
iris 24
pupil 25
true luminance point 30
false luminance point 31
luminance point 35
seeking region 36

BEST MODE FOR CARRYING OUT THE INVENTION

FIG. 1 shows a structure of an embodiment mode in which the present invention is embodied under best condition. In FIG. 1, a person 10 to be photographed is, for example, a user who uses a personal computer, or a car driver, and corresponds to a user who wears spectacles 11. A photographing camera 12 is arranged in front of the person to be photographed and in a substantially front view at such a position which is lower than a height position (horizontal position) of eyes of the person 10 to be photographed. This positioning reason is given as follows: That is, if the photographing camera 12 is arranged at another position which is the same height of the eyes, or is higher than the height of the eyes, then images of the eyes are overlapped with images of "eyelashes." As a result, there is a risk that processing operations of these images become complex (refer to FIG. 3E to FIG. 3H).

A light source 13 utilizes a light source constructed of an infrared light emitting diode (LED). A position of the light source 13 corresponds to a position which is separated from an optical axis 14 of the photographing camera 12, and is arranged at a position lower than the position of the photographing camera 12. In other words, if a distance "d" of FIG. 1 is small, then luminance brightness of a pupil is fluctuated in such a way that the pupil is photographed under light condition, or under dark condition, and therefore, it is difficult that the pupil is determined from a photographed image. As a consequence, the distance "d" is arranged at such a position that a dark pupil effect occurs, or in other words the person's pupils will appear dark in the photographed image. Also, the position of the light source 13 is arranged at a position lower than the position of the photographing camera 12. This positioning reason is given as follows: That is, a "false luminance point" which is reflected from a lens plane of the spectacles is easily discriminated from a "true luminance point." If the position of the light source 12 is lowered, then the true luminance point is located inside the pupil even in such a case where the eyes of the person 10 to be photographed are directed to an upper direction, or to a lower direction, whereas the false luminance point does not appear in the vicinity of the pupil (refer to FIG. 2A to FIG. 2D).

Figure 2:
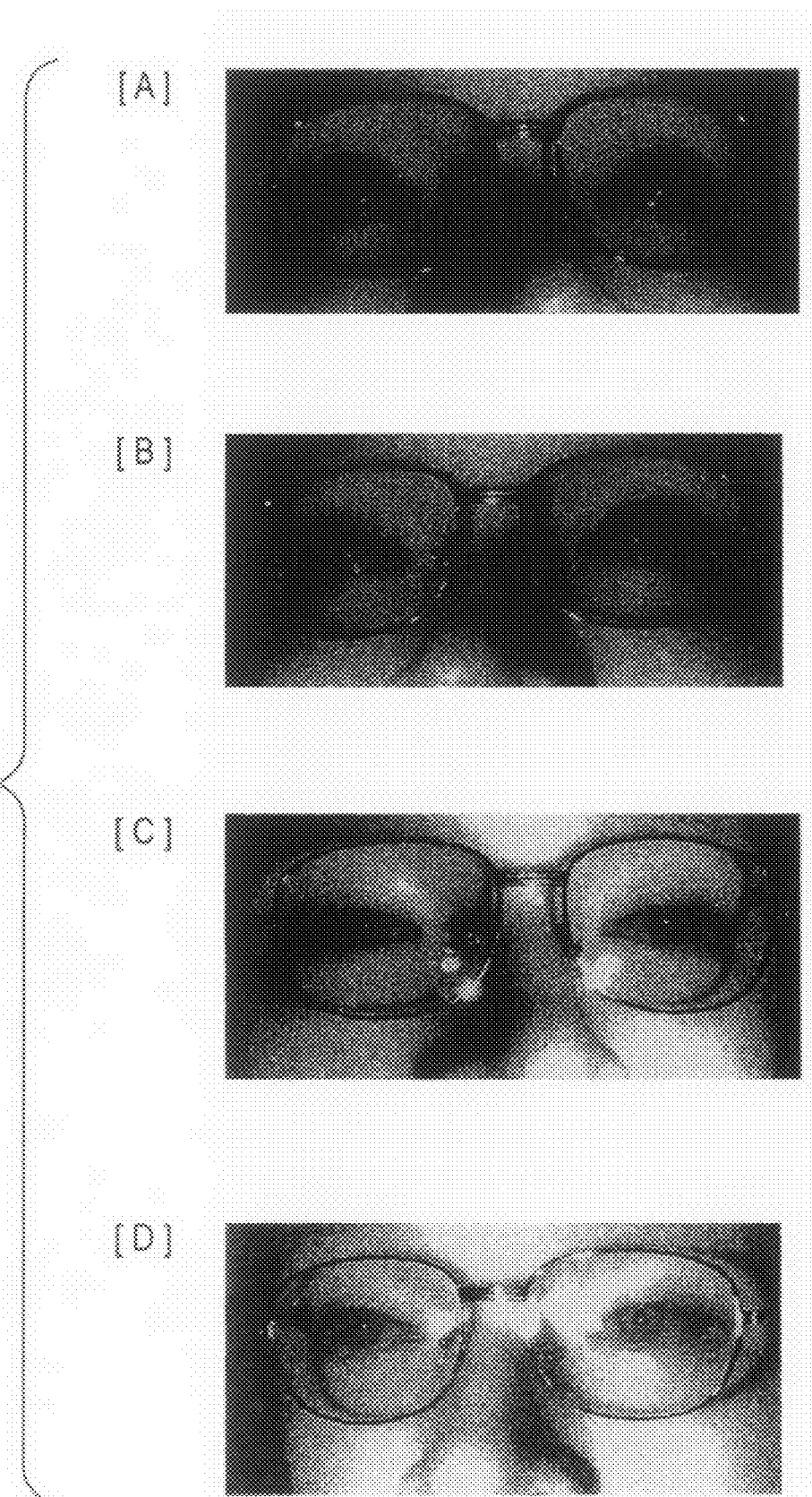
FIG. 2A shows a photographed image in the case where a person to be photographed is directed to an upper left direction when an infrared light source is installed at a position lower than a camera.
FIG. 2B indicates a photographed image in the case where the person to be photographed is directed to an upper right direction when the infrared light source is installed at the position lower than the camera.
FIG. 2C shows a photographed image in the case where the person to be photographed is directed to a lower left direction when the infrared light source is installed at the position lower than the camera.
FIG. 2D shows a photographed image in the case where the person to be photographed is directed to a lower right direction when the infrared light source is installed at the position lower than the camera.

FIG. 2A to FIG. 2D show an example of photographed images in the case that infrared light emitting diodes 13 are installed at positions lower than the photographing camera 12. FIG. 2A is a photographed image (photograph) in such a case that the person 10 to be photographed is directed to an upper left direction; FIG. 2B is a photographed image (photograph) in such a case that the person 10 to be photographed is directed to an upper right direction; FIG. 2C is a photographed image (photograph) is such a case that the person 10 to be photographed is directed to a lower left direction; and FIG. 2D is a photographed image (photograph) in such a case that the person 10 to be photographed is directed to a lower right direction. As apparent from these drawings, any of true luminance points are produced inside pupils 25, and false luminance points are produced outside the pupils 25.

Figure 3:
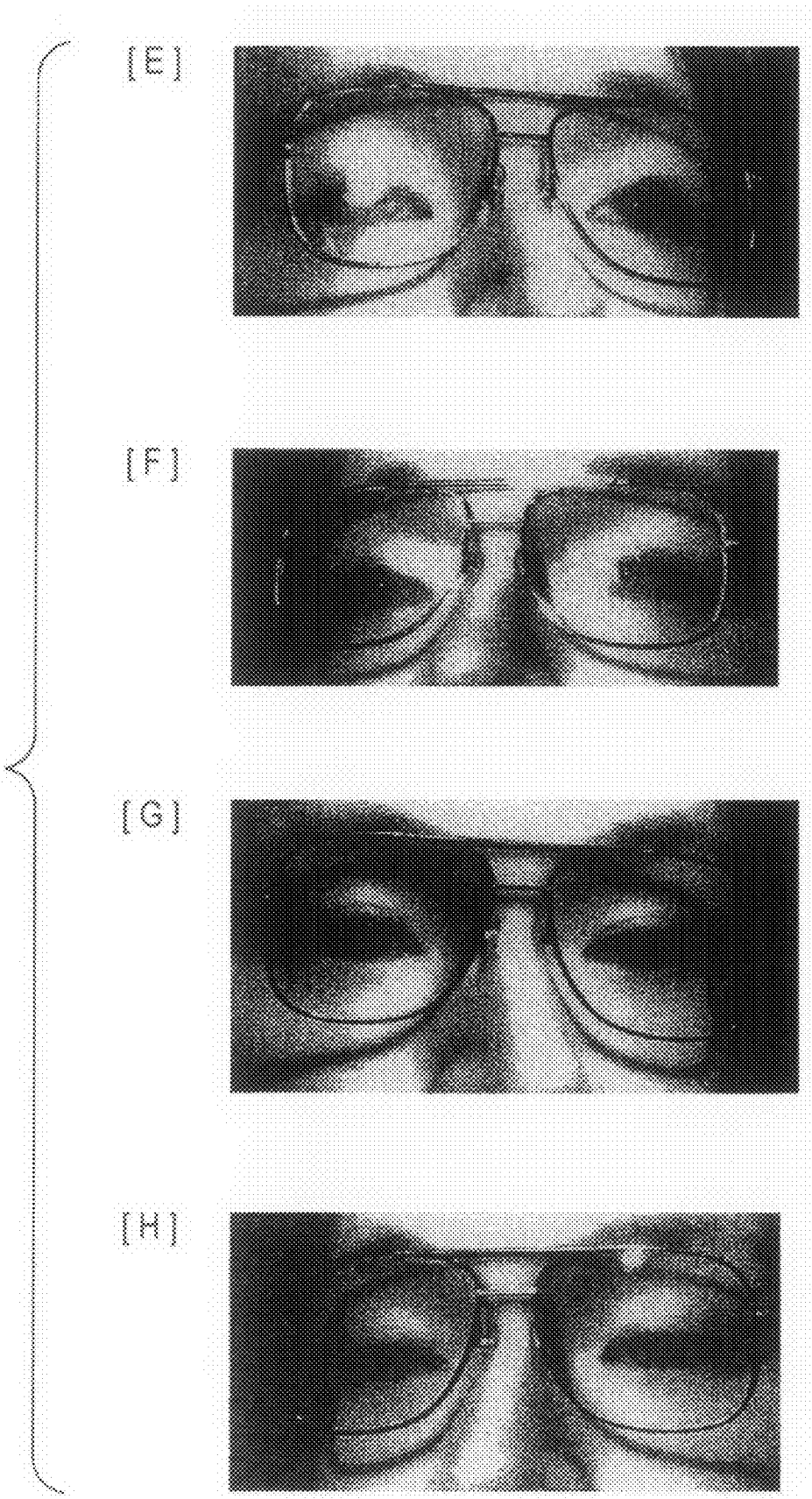
FIG. 3E shows a photographed image in the case where the person to be photographed is directed to an upper left direction when the infrared light source is installed at the position higher than the camera.
FIG. 3F shows a photographed image in the case where the person to be photographed is directed to an upper right direction when the infrared light source is installed at the position higher than the camera.
FIG. 3G shows a photographed image in the case where the person to be photographed is directed to a lower left direction when the infrared light source is installed at the position higher than the camera.
FIG. 3H shows a photographed image in the case where the person to be photographed is directed to a lower right direction when the infrared light source is installed at the position higher than the camera.

Conversely, FIG. 3E to FIG. 3H represent an example as to photographed images in the case that the position of the light source 13 is arranged at a position higher than the position of the photographing camera 12. FIG. 3E is a photographed image (photograph) in such a case that the person 10 in to be photographed is directed to an upper left direction; FIG. 3F is a photographed image (photograph) in such a case that the person 10 in to be photographed is directed to an upper right direction; FIG. 3G is a photographed image (photograph) in such a case that the person 10 to be photographed is directed to a lower left direction; and FIG. 3H is a photographed image (photograph) in such a case that the person 10 to be photographed is directed to a lower right direction. When the person 10 to be photographed is directed to the upper direction, as can be understood from FIG. 3E and FIG. 3F, false luminance points appear in the vicinity of the pupil 25, or collide with the pupil 25, so that either a true luminance point or the pupil 25 can be hardly detected. When the person 10 to be photographed is directed to the lower direction, and can be understood from FIG. 3G and FIG. 3H, true luminance points are excessively approached to eyelashes. As a result, there are some cases that the pupils 25 can be hardly detected.

The infrared light emitting diodes 13 are provided on both sides of an optical axis of the camera. This reason is given as follows: That is, if the infrared light emitting diode 13 is provided on one side of the optical axis 14 (for example, when infrared light emitting diode 13 is provided on left side), when the person 10 to be photographed is directed to such a side (namely, right side) that the light emitting diode 13 is not provided, there is such a problem that the true luminance point is deviated from the pupil 24.

A computer 15 connected to an output terminal of the photographing camera 12 contains a preprocessing unit 16, an image processing unit 17, and a calculating unit 18. The preprocessing unit 16 performs a preliminary processing operation in order to easily carry out processing operations of image data, for example, an adjustment of luminance brightness, an adjustment of contrast, an elimination of noise, and the like. The image processing unit 17 detects a true luminance point with respect to an acquired image, performs a process operation for calculating a center of a pupil, and furthermore, performs a process operation for calculating a center of a cornea ball (not shown) by utilizing knowledge data of morphology. It should be noted that since the preprocessing unit 16 utilizes the conventional technique and is not especially described in detail, a detailed explanation thereof is omitted. Since a portion of the process operations executed by the image processing unit 17 is coincident with the contents described in the patent publication 2, different points thereof will be mainly described. Since the process operations of the calculating unit 18 are coincident with the contents described in the patent publication 2, the above-described process operations will be simply described.

Figure 4:
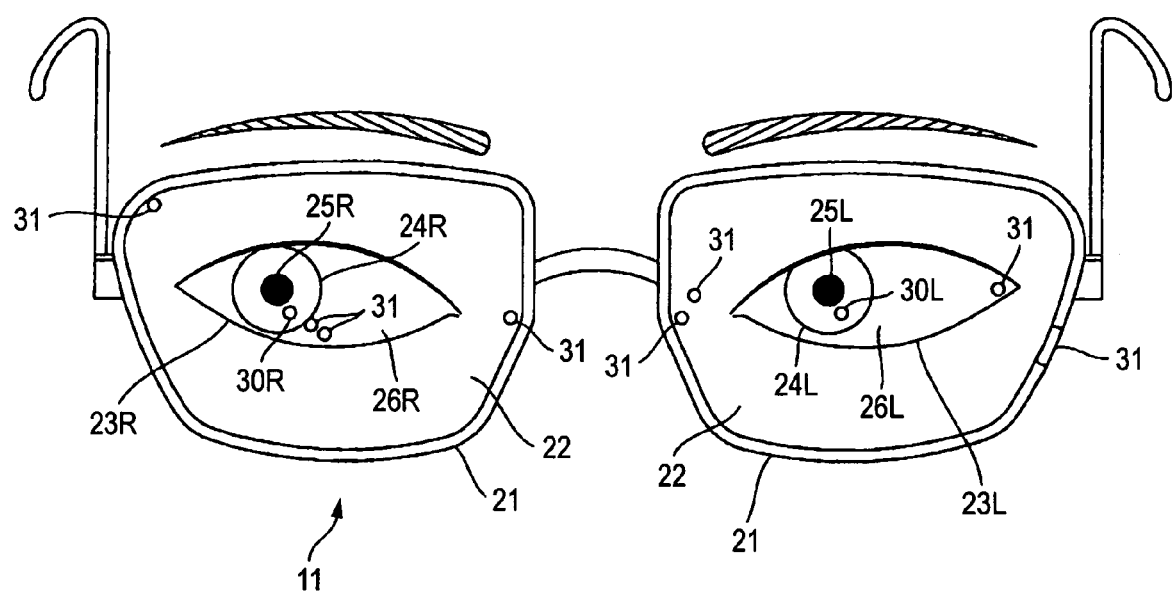
FIG. 4 represents an image for explaining an extraction of a major portion.

FIG. 4 indicates one example as to a photographed image of portions of spectacles 20 which are used by the person 10 to be photographed, corresponds to photographed image data in which main points on the present invention are extracted to be represented. In FIG. 4, the spectacles 11 are arranged by frames 21 and lenses 22. A right eye 23R and a left eye 23L appear inside the lenses 22. While irises 24 (24R, 24L) appear inside white eyeballs 26 (26R, 26L) of eyes 23 (23R, 23L), pupils 25 (25R, 25L) appear at substantially centers of the irises 24 (24R, 24L). The luminance brightness of the pupils 25 is dark, as compared with that of the irises 24. Also, the white eyeballs 26 are white color and have large luminance brightness. The irises 24 are light purple color (or light brown color), and have larger luminance brightness than that of the pupils 25, and smaller luminance brightness than that of the white eyeballs 26. Furthermore, true luminance points (namely, luminance points which can satisfy predetermined requirement, are used in order to calculate sight line vector) appear inside, or in the vicinity of the pupils 25, and also, false luminance points 31 appear which are reflected on portions of the lenses 22, or portions (metal members) of the spectacles 11. In other words, true luminance point(s) are luminance point(s) in the photographed image data of a person's face or eyes which correspond to the pupil(s) even when the person is wearing spectacles and different, false luminance point(s) appear in the photographed image data in close proximity to the true luminance point(s) due to reflection of light from the lenses or metal portion(s) of the spectacles.

Figure 5:
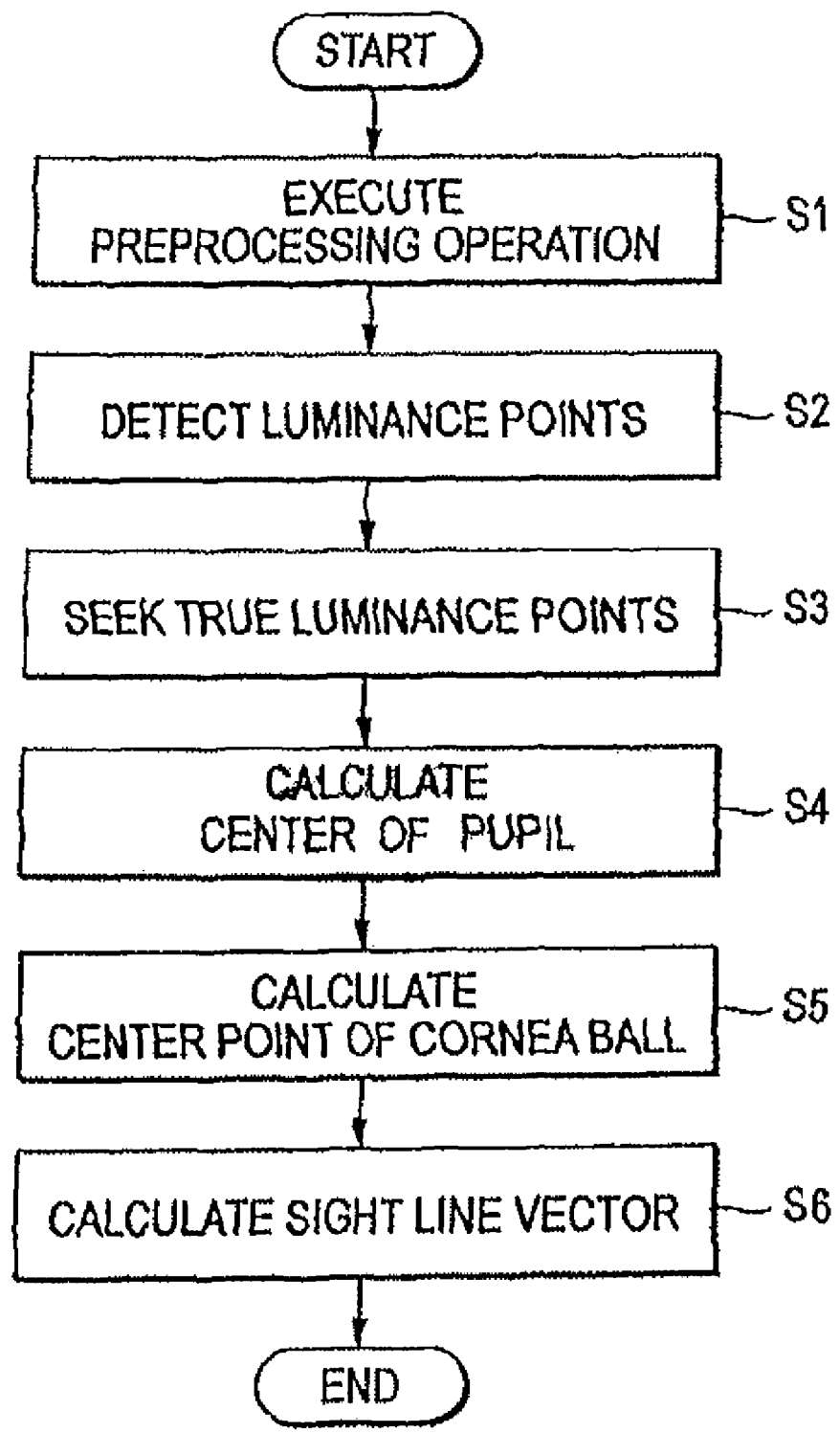
FIG. 5 is a flow chart for describing sequential operations executed by an image processing unit of the sight line vector detecting system.
Figure 6:
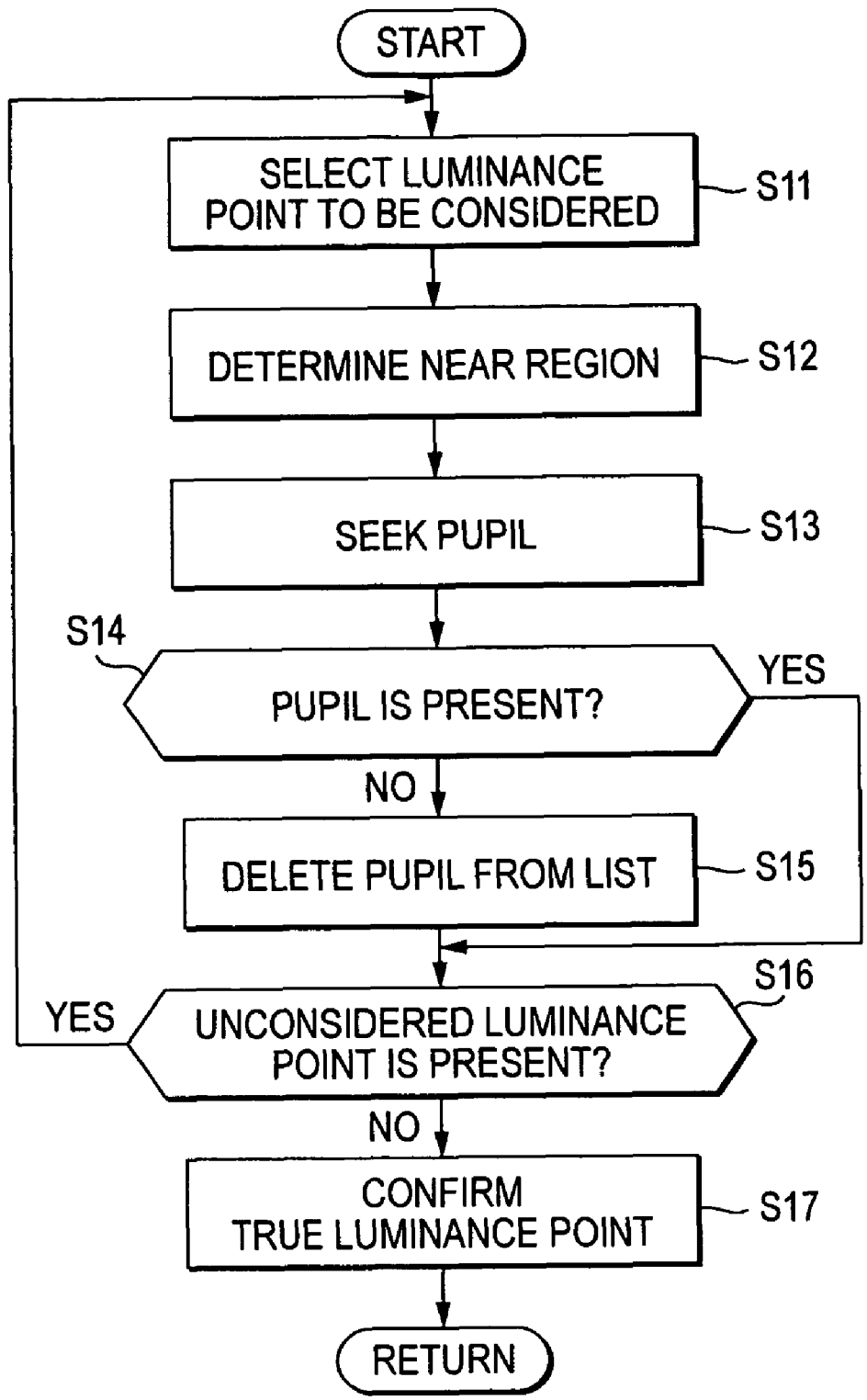
FIG. 6 is a flow chart for explaining sequential operations for acquiring a true luminance point.

FIG. 5 and FIG. 6 indicate for flow charts for describing sequential process operations executed in both the image processing unit 17 and the calculating unit 18. In FIG. 5, in a step S1, in order to easily perform process operations of the photographed image (FIG. 4), preliminary process operations are carried out, for instance, an adjustment of luminance brightness as to the entire photographed image; an adjustment of contrast; an elimination of noise. In a step S2, a bright point (or small region) whose luminance brightness is larger than, or equal to a constant value is acquired from the photographed image data so as to be defined as a luminance point, and thereafter, all of luminance points (30, 31) are acquired. In a step S3, a true luminance point (30) is determined from the luminance points acquired in the step S2. A step for acquiring a true luminance point is indicated in FIG. 6, which will be later described in detail. In a step S4, a center of the pupil (25) is calculated. The center of the pupil is calculated by utilizing such a calculation result that a contour of the pupil has been calculated when the true luminance point is acquired in the step S2.

In a step S5, a center point of the cornea ball (not shown) is calculated. A method of calculating a center of a cornea ball is described in detail in the patent application (patent publication 2) filed by the present applicant. Also, in this embodiment mode, the completely same method has been used. That is to say, in accordance with the knowledge given in the morphology, (1) distances measured from a right eye and a left eye to a nose are equal to each other; and (2) a ratio of a distance between the right and left eyes to a distance from one eye to the nose is a constant value (known value). Furthermore, (3) a distance between the right and left eyes is known; and (4) a central radius of a cornea ball is a constant value (known). Also, it may be alternatively determined that a focal distance (f) of the camera 12 and a camera parameter matrix (k) are known (these data may be measured before use). As a consequence, a distance from the image plane of the photographing camera 12 up to the eyes (or face surface) of the person 10 to be photographed may be calculated based upon these conditions. When the light emitting points of the infrared high sources 13 are located sufficiently near the photographing camera 12, both coordinates as to the center point of the cornea ball and coordinates as to the center point of the pupil 24 may be readily obtained by performing a high precision approximate calculation. In order to execute the above-explained calculation, it is so assumed that changes in the true luminance point 30 on the photographed image and also in the center position of the pupil 24 can be neglected, while these changes are caused by that the spectacles are used.

In a step S6, a sight line vector (or sight line direction) is calculated based upon the coordinates as to the center point of the pupil 24 and the coordinates as to the center point of the cornea ball, which are calculated in the step S5.

Figure 7:
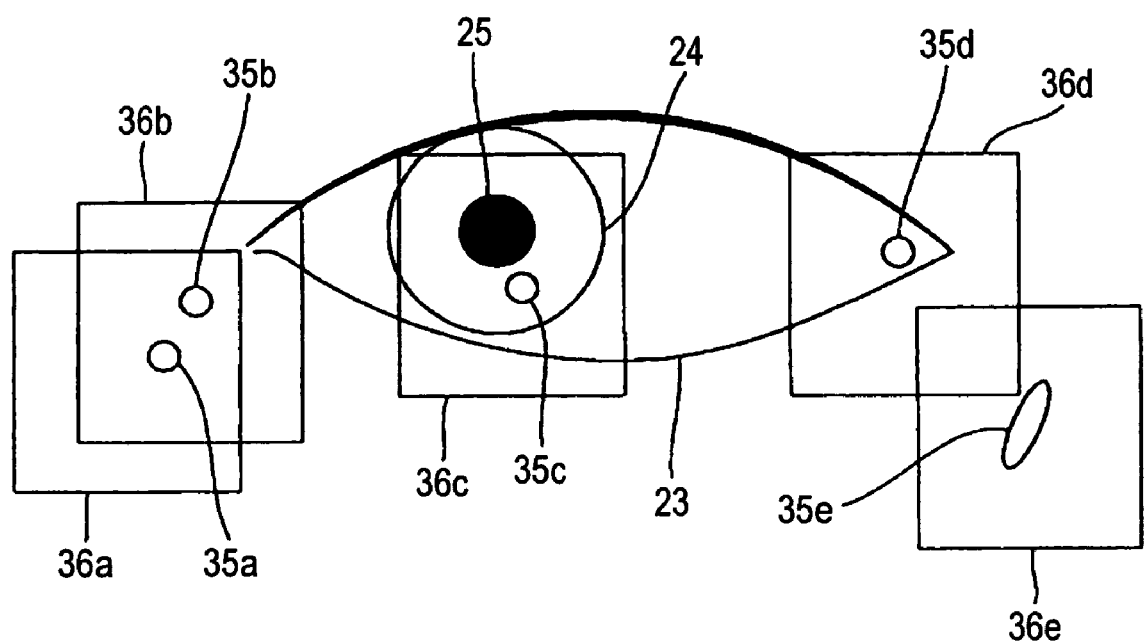
FIG. 7 is a diagram for seeking the true luminance point.

FIG. 6 shows seeking sequential operations (flow chart) for acquiring a true luminance point. As a requirement for a true luminance point, such a luminance point is conceived which can satisfy the below-mentioned conditions: (1) the luminance point has luminance brightness larger than, or equal to a predetermined value; (2) the dimension of the luminance point is smaller than a circle having a predetermined radius; (3) a pupil is located in the vicinity of the luminance point, or the luminance point is located within the pupil; (4) a distance between a right luminance point and a left luminance point is defined within a predetermined range. Assuming now that the above-described requirements (1) and (2) have already been satisfied, in FIG. 6, considering sequential operations as to the item (3) will now be explained. In a step S11, such a luminance point which will be considered is selected from a list of plural luminance points (for example, luminance points 35a to 35e of FIG. 7). In other words, a luminance point capable of satisfying a predetermined requirement as the true luminance point among multiple luminance points disposed in close proximity to each other in said photographed image data is selected. In a step S12, regions 36 (36a to 36e) having such a dimension capable of approximately containing the pupil 25 are determined with respect to the selected luminance points. In a step S13, a seeking operation is made as to whether or not the pupil 25 is contained within the regions 36. In this case, as to the pupil 25, luminance brightness thereof is smaller than, or equal to a predetermined value, namely dark; a radius thereof is located within a predetermined range; and a shape thereof is substantially circular.

In a step S14, a check is made as to whether or not the pupil 25 is present. In the case that the pupil is not present, the pupil is deleted from the list (step S15). The checking operation as to whether or not the pupil 25 is present is carried out as follows: That is, firstly, a dark region whose luminance brightness is small is sought, and then, a judgment is made as to whether or not this region is a circle. In order to judge the circle, the conventional technique is employed. For instance, while a boundary of a region is traced, if angle changes in tangential line vectors are substantially uniform and an end point is made coincident with a starting point, then it is possible to judge that this region is a circle. When the region is judged as the circle, a check is made as to whether or not a diameter of this region is present within a predetermined range. In the case where the pupil 25 is present, another check is made as to whether or not an unconsidered luminance point is present (step S16). When the unconsidered luminance point is present, the process operations from the step S11 to the step S15 are repeatedly carried out. In a step S17, a consideration is performed as to whether or not other requirements (for example, above-described fourth requirement) can be satisfied, and a true luminance point is confirmed so as to be determined.

While the embodiment mode of the present invention has been described in detail based upon the drawings, the technical scope of the present invention is not limited only thereto. For instance, the requirements for determining the true luminance point are not limited only to those described in the embodiment mode, but may be alternatively determined by other expressions if the contents of these expressions are essentially equal to the above-described requirements. Although it may be seen that the present embodiment mode is limited only to the person who wears the spectacles, the present invention may be alternatively applied to any person who wears no spectacles. In other words, if luminance points are present as one right luminance point and one left luminance point and correspond to true luminance points, then it may be judged that a checked person is a person who wears no spectacles, and a sight line vector may be acquired. Conversely, in such a case that there are large numbers of luminance points, it may be judged that the checked person is a person who wears spectacles.

The present patent application has been made based upon Japanese Patent Application (JP-2004-283456) filed on Sep. 29, 2004, the contents of which are incorporated herein as references.

The invention claimed is:

1. A sight line vector detecting system comprising:
an infrared light source for illuminating either an eye or a face;
a camera for photographing either the eye or the face; and
a computer configured to process photographed image data of said camera so as to calculate a sight line vector; wherein:
said computer detects both a true luminance point and a center of a pupil from said photographed image data so as to calculate the sight line vector, wherein said true luminance point is determined as a luminance point in the photographed image data which corresponds to a pupil of the eye regardless of whether the person is wearing spectacles, and even when a different luminance point also appears in the photographed image data in close proximity to the true luminance point due to reflection of light from a portion of the spectacles,
said photographing camera is installed at a front view of the face of a person to be photographed, and at a position lower than the position of the eye, and
said infrared light source is provided on both a right side and a left side of an optical axis of said photographing camera.

2. A sight line vector detecting system as claimed in claim 1 wherein:
said infrared light source is installed at a position on both the right side and the left side of the optical axis of said photographing camera in such a manner that the person's pupil will appear dark in the photographed image data.

3. A sight line vector detecting system as claimed in claim 1 wherein:
said infrared light source is installed at a position lower than said photographing camera.

4. A sight line vector detecting system as claimed in claim 1 wherein:
said computer includes an image processing unit for detecting both the true luminance point and the center of the pupil from said photographed image data; and a calculating unit for calculating the sight line vector; and wherein:
said image processing unit performs a processing operation that determines a luminance point capable of satisfying a predetermined requirement as the true luminance point among multiple luminance points disposed in close proximity to each other in said photographed image data, calculates the center of said pupil, and further, calculates a center of a cornea ball by utilizing data obtained based upon knowledge of morphology.

5. A sight line vector detecting system as claimed in claim 1 wherein:
said calculating unit calculates the sight line vector based upon said center of the pupil and a center of a cornea ball.

6. A sight line vector detecting system as claimed in claim 1 wherein:
said computer further comprises: a preprocessing unit for preprocessing said photographed image data.

7. A sight line detecting method using a sight line vector detecting system equipped with an infrared light source for illuminating either an eye or a face, a camera for photographing either the eye or the face, and a computer configured to process photographed image data of said camera so as to calculate a sight line vector, the method comprising the steps of:
illuminating either the eye or the face with the infrared light source;
photographing either the eye or the face which is illuminated using said camera;
processing the photographed image data of said camera using said configured computer so as to calculate said sight line vector, wherein said processing comprises the steps of:
detecting both a true luminance point and a center of a pupil from said photographed image data, wherein said true luminance point is determined as a luminance point in the photographed image data which corresponds to a pupil of the eye regardless of whether the person is wearing spectacles, and even when a different luminance point also appears in the photographed image data in close proximity to the true luminance point due to reflection of light from a portion of the spectacles; and
calculating a sight line vector,
wherein said photographing camera is installed at a front view of the face of a person to be photographed, and at a position lower than the position of the eye, and
said infrared light source is provided on both a right side and a left side of an optical axis of said photographing camera.

8. A sight line detecting method as claimed in claim 7 wherein:
said detecting step involves:
determining a luminance point capable of satisfying a predetermined requirement as the true luminance point among multiple luminance points disposed in close proximity to each other in said photographed image data, and calculating the center of said pupil; and
calculating a center of a cornea ball by utilizing data obtained based upon knowledge of morphology.

9. A sight line detecting method as claimed in claim 8 wherein:
said sight line vector calculating step calculates the sight line vector based upon said center of the pupil and said center of the cornea ball.

10. A sight line detecting method as claimed in claim 7 further comprising:
a step for preprocessing said photographed image data before said detecting step.

11. A sight line vector detecting system as claimed in claim 2 wherein:
said infrared light source is installed at a position lower than said photographing camera.

12. A sight line vector detecting system as claimed in claim 2 wherein:
said computer includes an image processing unit for detecting the true luminance point and the center of the pupil from said photographed image data; and a calculating unit for calculating the sight line vector; and wherein:
said image processing unit performs a processing operation that determines a luminance point capable of satisfying a predetermined requirement as the true luminance point among multiple luminance points disposed in close proximity to each other in said photographed image data, calculates the center of said pupil, and further, calculates a center of a cornea ball by utilizing data obtained based upon knowledge of morphology.

13. A sight line vector detecting system as claimed in claim 3 wherein:
said computer includes an image processing unit for detecting the true luminance point and the center of the pupil from said photographed image data; and a calculating unit for calculating the sight line vector; and wherein:
said image processing unit performs a processing operation that determines a luminance point capable of satisfying a predetermined requirement as the true luminance point among multiple luminance points disposed in close proximity to each other in said photographed image data, calculates the center of said pupil, and further, calculates a center of a cornea ball by utilizing data obtained based upon knowledge of morphology.

14. A sight line vector detecting system as claimed in claim 6 wherein:
said computer includes an image processing unit for detecting the true luminance point and the center of the pupil from said photographed image data; and a calculating unit for calculating the sight line vector; and wherein:
said image processing unit performs a processing operation that determines a luminance point capable of satisfying a predetermined requirement as the true luminance point among multiple luminance points disposed in close proximity to each other in said photographed image data, calculates the center of said pupil, and further, calculates a center of a cornea ball by utilizing data obtained based upon knowledge of morphology.

15. A sight line vector detecting method as claimed in claim 7 wherein:
said infrared light source is installed at a position on both the right side and the left side of optical axis of said photographing camera in such a manner that the person's pupil will appear dark in the photographed image data.

* * * * *